United States Patent

Herwig et al.

[11] Patent Number: 5,789,643
[45] Date of Patent: Aug. 4, 1998

[54] PROCESS FOR OLIGOMERIZING I-BUTENE COMPRISING HYDROISOMERIZING PORTION OF CONDENSATE AND RECYCLING THE HYDROISOMERATE TO FRACTIONATION

[75] Inventors: Jens Herwig, Köln; Hans-Jürgen Bister, Neuss; Arnd Stüwe, Leverkusen, all of Germany

[73] Assignee: EC Erdolchemie GmbH, Cologne, Germany

[21] Appl. No.: 960,910

[22] Filed: Oct. 30, 1997

[30] Foreign Application Priority Data

Nov. 11, 1996 [DE] Germany ............... 196 46 405.6

[51] Int. Cl.$^6$ ............... C07C 2/02; C07C 1/00
[52] U.S. Cl. ............... 585/518; 585/314; 585/324; 585/326; 585/329
[58] Field of Search ............... 585/518, 314, 585/324, 326, 329

[56] References Cited

U.S. PATENT DOCUMENTS

| | | | |
|---|---|---|---|
| 4,132,745 | 1/1979 | Amigues et al. | 260/683.2 |
| 4,777,322 | 10/1988 | Hoelderich et al. | 585/666 |
| 5,416,176 | 5/1995 | Hunt | 585/326 |
| 5,674,955 | 10/1997 | Kerr et al. | 585/518 |

FOREIGN PATENT DOCUMENTS

| | | | |
|---|---|---|---|
| 735727 | 1/1970 | Belgium. | |
| 930382 | 7/1973 | Canada | 260/696 |
| 0170182 | 2/1986 | European Pat. Off. | C07C 11/08 |

OTHER PUBLICATIONS

W. Krönig, et al.: "Oligomerisierung von Butenen", Erdöl und Kohle Erdgas Petrochemie., Bd. 19, Nr. 7, Jul. 1966, Leinfelden DE, pp. 497–500, XP002053199.

G. Scharfe, Convert Butenes to high octane oligomers, Hydrocarbon Processing, 52, 4, pp. 171–173, (1973).

*Primary Examiner*—Glenn Caldarola
*Assistant Examiner*—In Suk Bullock
*Attorney, Agent, or Firm*—Sprung Kramer Schaefer & Briscoe

[57] ABSTRACT

The i-butene present in a $C_4$ raffinate I is subjected in a first step to a first hydroisomerization. The hydroisomerization product is subjected to fractional distillation, with essentially 2-butene and n-butane being obtained as bottom product and i-butene and i-butane being obtained as overhead product. The overhead product is condensed and the condensate is divided into two parts. One part is subjected to a second hydroisomerization and the second hydroisomerate is recycled to the upper third of the fractionation column. The other part of the condensed overhead product is fed to the oligomerization. The condensed overhead-product of the fractionation column is divided in such a manner that, based on 1 part by volume of condensate conducted to the oligomerization, 1–5 parts by volume are fed to the second hydroisomerization.

11 Claims, 1 Drawing Sheet

PROCESS FOR OLIGOMERIZING I-BUTENE COMPRISING HYDROISOMERIZING PORTION OF CONDENSATE AND RECYCLING THE HYDROISOMERATE TO FRACTIONATION

BACKGROUND OF THE INVENTION

1. Field of the Invention

The present invention relates to a process for oligomerizing i-butene which is present in a $C_4$ raffinate I, and comprises the steps of a first hydroisomerization of the $C_4$ raffinate I, a subsequent separation of 2-butene and n-butane by distillation, a second hydroisomerization of part of the overhead product of the separation by distillation, the reaction product of which is recycled to the separation by distillation, and finally the actual oligomerization of the i-butene of the residual overhead product of the separation by distillation.

The oligomers of i-butene are predominantly diisobutylene ($C_8$), triisobutylene ($C_{12}$), tetraisobutylene ($C_{16}$), pentaisobutylene ($C_{20}$) and others whose proportions decrease constantly with increasing degree of oligomerization. Oligomers of this type still contain one double bond each; they are chiefly completely hydrogenated and then serve as absolutely aromatic-free solvents of the higher boiling ranges in the cosmetic and pharmaceutical industries. Aromatic-free solvents of this type can otherwise be obtained only with difficulty and thus expensively. The nonhydrogenated hydrogenated oligomers which still contain a double bond can further be fed to the oxo synthesis or esterification, with, from diisobutene (DIB)for example, isononyl alcohol and, further, dinonyl phthalate being prepared, or, with direct esterification of DIB, dioctyl phthalate, which are used as plasticizers for thermoplastics. Triisobutene can, in addition, be processed to give dodecylmercaptan, a rubber processing aid. Finally, the addition of dimeric butenes, or octanes derived therefrom by hydrogenation, to engine fuel may be mentioned.

2. Description of the Related Art

It is already known to oligomerize butenes on acid catalysts, such as acid ion exchangers. (Erdöl und Kohle, Erdgas, Petrochemie 19 (1966), 497–500; Hydrocarbon Processing 1973, 171–173). A disadvantage in such processes is the simultaneous formation of what is termed codimer from one molecule each of i-butene and 1-butene. This codimer has less-desirable properties and thus represents a source of loss for the oligomers of i-butene. An effective suppression of this codimer would only be possible if 1-butene were successfully separated off from the $C_4$ raffinate I. However, a separation of this type is not possible with reasonable expenditure on account of the extraordinarily narrow boiling range of i-butene and 1-butene. The object is therefore to remove 1-butene in order to be able to isolate i-butene. A possibility for this is offered by isomerizing 1-butene to give 2-butene (cis and trans), which can be separated off from i-butene by distillation. However, as described in U.S. Pat. No. 4,132,745, a hydroisomerization of this type is only successful to residual 1-butene contents of approximately 2.5% by weight.

SUMMARY OF THE INVENTION

It has now been found that the $C_4$ raffinate can be substantially freed from 1-butene, so that in the subsequent oligomerization, advantageous effects with regard to the yield of oligomerization products can be achieved and the oligomer spectrum can be shifted to higher oligomers.

The invention relates to a process for oligomerizing i-butene present in a $C_4$ raffinate I, which comprises a) subjecting the $C_4$ raffinate I to a first hydroisomerization on a noble metal catalyst, with 30–80° C., 5–30 bar, an LHSV of 5–30 h$^{-1}$ and a rate of 3–20 L (S.T.P.) of gaseous $H_2$ per liter of $C_4$ raffinate I which exceeds the amount of $H_2$ required to hydrogenate highly unsaturated components in the $C_4$ raffinate being employed, b) subjecting the hydroisomerization product of a) to fractional distillation, 5–25 bar and the temperature established at this pressure being employed, and 2-butene and n-butane being taken off as bottom product and i-butene and i-butane as overhead product, c) condensing the overhead product of b), dividing it into two parts and subjecting the first part to a second hydroisomerization on a noble metal catalyst, with 30–80° C., 5–30 bar, an LHSV of 5–30 h$^{-1}$ and a rate of 0.3–5 L (S.T.P.) of gaseous $H_2$ per liter of $C_4$ raffinate I being employed and the hydroisomerization conditions in a) and c) being identical or different, and the hydroisomerization product of c) being recycled into the upper third of the fractionation column of b) and d) oligomerizing the second part of the condensed overhead product of b) at 30–140° C. on an acid catalyst.

BRIEF DESCRIPTION OF THE DRAWING

The accompanying drawing represents an embodiment of the inventive process showing a first hydroisomerization reactor A, a distillation column B, a second hydroisomerization reactor C and an oligomerization reactor D. In accordance with the invention the overhead distillation product in line 5 is divided into one part through line 9 which is further processed in reactor D, and into a second part through line 6 which is again hydroisomerized in reactor C and thereafter again distilled in the distillation column B.

DETAILED DESCRIPTION OF THE INVENTION

Figure 1:
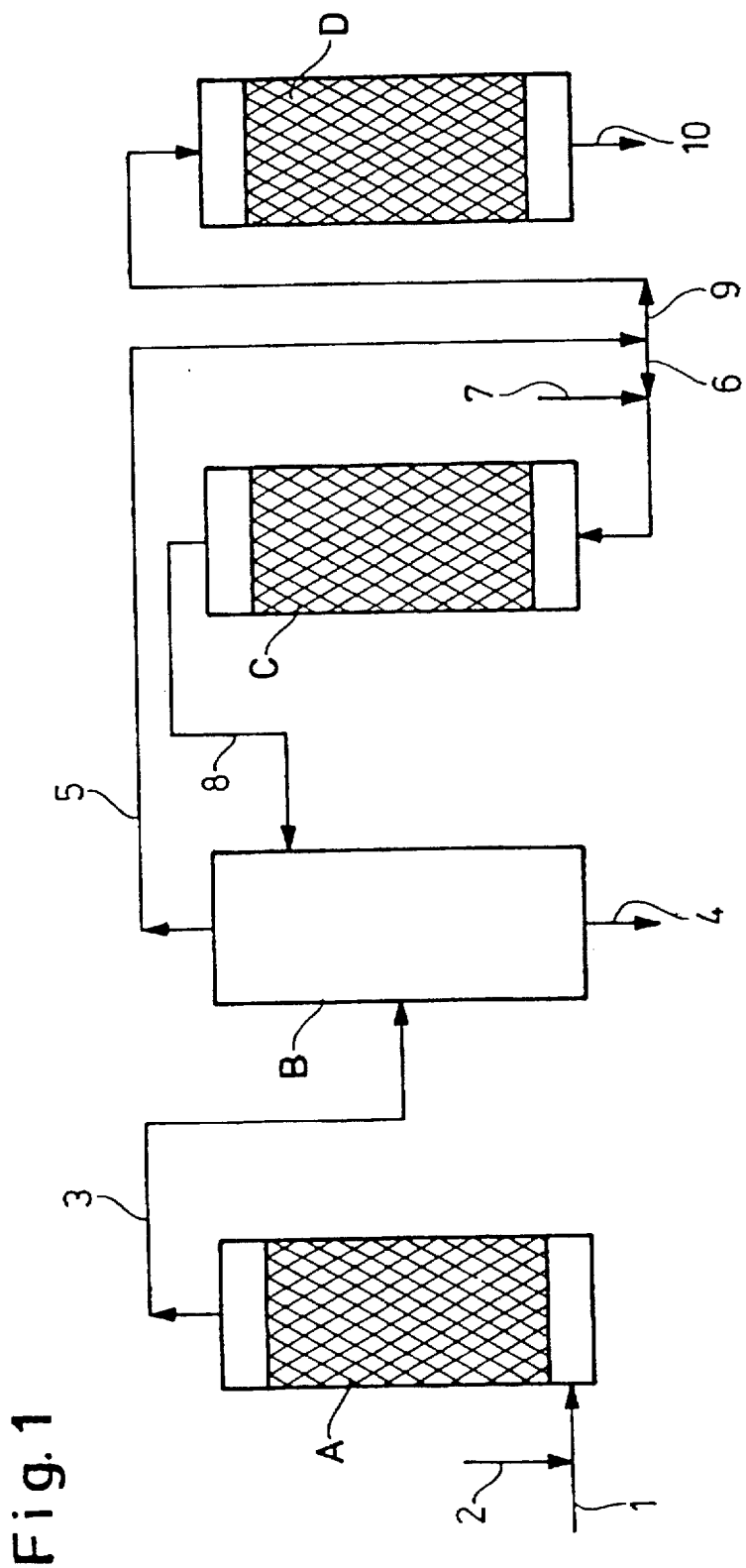

The $C_4$ raffinate I is obtained from the crude $C_4$ distillation fraction of a cracker product by removing the 1,3-butadiene present therein by extraction and further using it as material of value. In this extraction, other highly unsaturated hydrocarbons, such as vinylacetylene, 1,2-butadiene and other acetylene compounds are also removed from the crude $C_4$ distillation fraction. The $C_4$ raffinate I present after the extraction thereafter contains only minor amounts of highly unsaturated compounds. The numerically predominant contents in $C_4$ raffinate I are n-butane, i-butane, n-1-butene, 2-butene (cis and trans) and i-butene. In addition, $C_3$ and $C_5$ hydrocarbons may be present in insignificant amounts.

The first hydroisomerization as reaction step a) of the process according to the invention is carried out at a temperature of 30–80° C., preferably 40–60° C. and at a pressure of 5–30 bar, preferably 10–20 bar. An LHSV (Liquid Hourly Space Velocity) of 5–30 h$^{-1}$, preferably 7–20 h$^{-1}$, particularly preferably 7–12 h$^{-1}$, is set. The amount of added gaseous hydrogen must satisfy two tasks, that is, on the one hand, the complete removal of said highly unsaturated compounds and, on the other hand, the provision of an amount of $H_2$ recognized as optimum for the hydroisomerization. Monounsaturated $C_4$ hydrocarbons of the type already present in the $C_4$ raffinate I are produced from said highly unsaturated hydrocarbons in this case by partial hydrogenation under the hydroisomerization conditions. The amount of $H_2$ for removing the highly unsaturated $C_4$ hydrocarbons clearly depends on the extent of their presence and can readily be determined analytically and in a manner known to those skilled in the art. The further amount required in addition to this amount of $H_2$ is 2–15 L (S.T.P.) of gaseous $H_2$ per liter of $C_4$ raffinate I. Preferably, this amount of $H_2$ is 3–10 L (S.T.P.) of gaseous $H_2$ per liter of liquid $C_4$ raffinate I.

For the hydroisomerization, the $C_4$ raffinate I is present in the liquid phase. It can in this case be run over the catalyst from top to bottom in the trickling phase, or the flow passes through the reactor equipped with the catalyst from bottom to top, that is in flooded form. The gaseous hydrogen can also be conducted in concurrent flow or air countercurrent flow to the $C_4$ raffinate I. The preferred procedure is that with a flooded reactor, with the hydrogen being conducted in countercurrent flow.

Catalysts which are suitable for the hydroisomerization are all supported noble metal hydrogenation catalysts. Suitable noble metals in this case are: Ru, Rh, Pd, Ir and Pt, preferably Ru, Pd and Pt, particularly preferably Pd. Supports to which such noble metals can be applied are, for example, $Al_2O_3$ of the various modifications, $SiO_2$, carbon, kieselguhr and salts such as $BaSO_4$, inter alia. It has proved to be expedient to damp and thus optimize the activity of the noble metals of said type by adding sulfur compounds.

In reaction step b) of the process according to the invention, the hydroisomerization product of a) is subjected to fractional distillation. In this case, a pressure of 5–25 bar and the temperature established under distillation conditions at this pressure are employed. Typical temperatures which establish themselves at an operating pressure of 12 bar are 25° C. at the top of the column and 88° C. in the bottom of the column. A preferred pressure range is 10–20 bar. A lower pressure than the specified minimum value of 10 bar leads to further decreased top temperatures which, for the subsequent condensation, require an uneconomically expensive cooling medium. In a further preferred manner, the same pressure is employed in the reaction steps a), b) and c) of the process according to the invention, and only the temperatures required are adjusted.

The bottom product obtained in reaction step b) is a mixture which essentially comprises n-butane and 2-butene; the 2-butene here is that originally present in $C_4$ raffinate I and that formed by hydroisomerization from 1-butene. 2-Butene is a valuable feed stock for preparing gasoline alkylate, for the oxidation to give methyl ethyl ketone and finally, on recycling to the cracker, gives an increased yield of ethylene, compared with other $C_4$ hydrocarbons.

The overhead product of the distillation according to reaction step b) of the process according to the invention essentially comprises i-butene and i-butane and only minor amounts of 1-butene. It is condensed and then divided into two portions. The first part is fed to a second hydroisomerization (reaction step c)), which proceeds within the bounds of the conditions specified above for the first hydroisomerization. However, preferably, the LHSV is set to a higher trend in the second hydroisomerization step than in the first hydroisomerization step, for example generally to a value of 5–30 h$^{-1}$, preferably 10–25 h$^{-1}$, in agreement with the first hydroisomerization step, but particularly preferably 15–25 h$^{-1}$ for the second hydroisomerization step. In the second hydroisomerization reactor, also, the condensate can be run from top to bottom or from bottom to top, preferably from bottom to top, with the hydrogen here also being conducted in cocurrent stream or in countercurrent stream. The outflowing second hydroisomerizate is recycled to the upper third of the fractionation column, so that 2-butene, which is formed in the second hydroisomerization reactor, is additionally driven to the bottom of the fractionation column. The addition of fresh hydrogen can be selected to be lower than in the 1st isomerization, ie. 0.3–5 L (S.T.P.) of $H_2$ per 1 of liquid $C_4$, since highly unsaturated compounds no longer need be expected in the second hydroisomerization reactor, so that a proportion of hydrogen to be used in addition for this can be omitted.

The ratio of the part-streams of the condensed overhead product of the fractionation column is set in such a manner that 10–40 parts by volume, preferably 20–30 parts by volume, are fed as a first part of the second hydroisomerization, based on 1 part by volume of the second part to which the oligomerization is fed. Since the second partial volume fed to the oligomerization corresponds, together with the bottom outlet of the fractionation column, to the total input of the $C_4$ raffinate I into the first hydroisomerization, a circulation through the second hydroisomerization reactor and the fractionation column is superimposed on the stream flowing through the process according to the invention, which circulation, in the manner described above, corresponds to 10–40 times the part-stream conducted to the oligomerization. The part-stream recirculated through the second hydroisomerization reactor thus has a higher trend. If the increased throughput through the second hydroisomerization reactor cannot be accommodated by the LHSV which is set higher, the capacity of this second hydroisomerization reactor is expediently increased. Obviously, the fractionation column must be designed to the higher throughput due to the superimposed circulation.

In the reaction step d) of the process according to the invention, the second part of the condensed overhead product is fed to the oligomerization. The oligomerization is carried out at 30–140° C. on an acid catalyst. As catalyst for the oligomerization, use is made of heterogeneous inorganic or organic catalysts, for example acid zeolites, silica gels and acid $Al_2O_3$, acid sheet and framework silicates, acid-coated support materials or gel-form or macroporous cation exchangers in the H$^+$form. Catalysts of this type are familiar to those skilled in the art and are offered on the market by various manufacturers.

The accompanying FIG. 1 shows an example of the procedure of the process according to the invention: liquid $C_4$ raffinate I, characterized by a content of i-butene to be oligomerized, is fed via line 1 to a first hydroisomerization reactor A, which is equipped with a fixed-bed noble metal hydrogenation catalyst. The required amount of $H_2$ is admixed via line 2 to the $C_4$ raffinate I. A is in the flooded state and the flow passes through it from bottom to top. The first hydroisomerate leaving A is passed via line 3 to the distillation column B, from which, as bottom product 4, a mixture is taken off which comprises as essential components n-butane and 2-butene. The overhead product which is taken off via line 5 and contains, in addition to principally i-butene and i-butane, only little 1-butene, is condensed and divided into two portions, which are fed via lines 6 and 9 to further treatment. The portion conducted via 6 is mixed with $H_2$ via line 7 and fed to a second hydroisomerization reactor C, which, as is A, is equipped with a fixed-bed noble metal hydrogenation catalyst and, likewise, the flow passes through from bottom to top. The second hydroisomerate from C is fed via line 8 to the upper part of B. The portion conducted via 9 is fed to the oligomerization reactor D, which is equipped with an acid catalyst, for example a cation exchanger in the H$^+$form. The portion conducted via 6 is generally considerably greater than the portion conducted via 9. The oligomerized material taken off via 10 is resolved into fractions having different degrees of oligomerization. Obvious additional apparatus and those known to those skilled in the art are not included in FIG. 1 for reasons of clarity; this concerns pumps, metering devices, temperature and pressure measurement points, preheaters, the condenser in line 5, the reflux device from 5 to B, the bottom reboiler at the lower part of B and the resolution of the oligomerized material subsequent to D.

The oligomerized material of the process according to the invention is primarily characterized by two advantages: firstly, in the region of the dimer (DIB=diisobutylene) there is an increase by more than 3% points, typically from 96% to over 99% of the total dimer content, whereas the proportion of the codimer, that is the dimer of i-butene and 1-butene, decreases. These codimers are, as already mentioned above, less desirable than DIB. Secondly, surprisingly, there is a shift of the entire oligomer spectrum from DIB to higher degrees of oligomerization, that is towards $C_{12}$, $C_{16}$ and $C_{20}$ hydrocarbons.

EXAMPLES

Example 1a (Hydroisomerization of 1-butene to 2-butene in $C_4$ raffinate I)

A hydroisomerization reactor, which, as A in FIG. 1 was connected to the other apparatuses shown in FIG. 1, was operated under the following conditions and gave the results listed in Tabs. 1 and 2: 200 ml of catalyst 0.3% by weight Pd on $Al_2O_3$ (Engelhard) were activated at 200° C. for 24 h with 200 l of $H_2$/h; 1150 g/h of $C_4$ raffinate I (LHSV=10); temp. 45° C. (reactor center); pressure 15 bar, 12 l/h of $H_2$.

TABLE 1

$C_4$ raffinate I feed and hydroisomerizate as a function of running time

| Running time | Feed | Hydroisomerizate | | | | |
|---|---|---|---|---|---|---|
| (days) | 0–7 days | 1 | 4 | 5 | 6 | 7 |
| i-butane | 4.59 | 4.8 | 4.9 | 4.82 | 4.91 | 4.85 |
| n-butane | 13.5 | 15.6 | 15.56 | 15.64 | 15.54 | 15.93 |
| i-butene | 42.0 | 42.01 | 42.11 | 42.18 | 42.18 | 41.22 |
| 1-butene | 23.6 | 4.65 | 4.38 | 4.13 | 3.98 | 3.81 |
| 2-butene (cis, trans) | 16.0 | 32.41 | 32.23 | 32.56 | 32.66 | 33.56 |
| 1,3-butadiene | 0.22 | 0.00 | 0.00 | 0.00 | 0.00 | 0.00 |
| Higher-boiling compounds | 0.09 | 0.08 | 0.08 | 0.09 | 0.08 | 0.09 |

Example 1b (Distillation)

A distillation column of length 8 m and diameter 50 mm, packed with 6 mm wire mesh rings (number of theoretical plates: 120), which as B was connected to the further apparatuses shown in FIG. 1, was continuously charged with 1150 g/h of hydroisomerate. At a pressure of 12 bar, a top temperature of 72° C. and a bottom temperature of 86° C., 305 g/h of overhead product, 8630 g/h of reflux and 845 g/h of bottom product were established.

Example 1c (second hydroisomerization)

The reflux from Example 1b, before it was recycled to the column, was passed via a hydroisomerization reactor, which as C was connected to the further apparatuses shown in FIG. 1. The following reaction conditions were set: 680 ml of catalyst 0.3% by weight of Pd on $Al_2O_3$ (Engelhardt), activated as under Example 1a. 8630 g/h reflux product from Example 1b (LHSV=22); temperature 48° C. (reactor center), pressure 12 bar, 10 l/h of $H_2$. The overhead product corresponded in composition to the feed from Example 1d.

Example 1d (oligomerization)

An oligomerization reactor, which was connected as D in FIG. 1 to the further apparatuses shown in FIG. 1, was operated under the following conditions and gave the results listed in Tab. 3: 167 mg of cation exchanger in $H^+$ form as catalyst; in the course of 60 min throughput of 100 g of the hydroisomerate according to the invention via line 9 according to FIG. 1 of composition 9.88% i-butane, 1.00% n-butane, 86.69% i-butene, 0.59% 1-butene, 1.62% 2-butene (cis, trans), 0.22% higher-boiling compounds at three different temperature conditions (experiments V1, V2, V3) and, for comparison, the same amount of a hydroisomerate not according to the invention without use of reactor C, of the composition 4.47% i-butane, 13.92% n-butane, 42.55% i-butene, 22.52% 1-butene, 16.06% 2-butene (cis, trans), 0.48% higher-boiling compounds (comparison experiment comp.).

TABLE 3

Oligomerized material and $C_4$ raffinate II calculated therefrom

| | V 1 | V 2 | V 3 | Comp. |
|---|---|---|---|---|
| Reactor temperature (°C., start) | 100–102 | 101–103 | 101–103 | 101–103 |
| Reactor temperature (°C., max.) | 122.3 | 113.3 | 125.6 | 105 |
| $C_4$ (Residual raffinate I) | 13.11% | 12.49 | 11.89 | 57.15 |
| $C_8$-hydrocarbons | 31.82 | 36.53 | 33.15 | 27.83 |
| $C_{12}$-hydrocarbons | 47.20 | 44.73 | 46.89 | 13.76 |
| $C_{16}$-hydrocarbons | 7.33 | 5.89 | 7.42 | 1.26 |
| $C_{20}$-hydrocarbons | 0.54 | 0.36 | 0.65 | — |
| Residual raffinate II | | | | |
| i-butane | 67.89 | 69.42 | 70.65 | 8.52 |
| n-butane | 7.78 | 7.93 | 8.16 | 25.73 |
| i-butene | 9.38 | 6.81 | 5.30 | 1.08 |
| 1-butene | 2.06 | 2.96 | 2.35 | 22.08 |
| 2-butene (cis, trans) | 12.89 | 12.88 | 13.54 | 42.34 |
| Higher-boiling compounds | — | — | — | 0.25 |

Taking the sum of the $C_8$–$C_{20}$ oligomers obtained as 100%, a distribution is obtained as in Tab. 4 below:

TABLE 4

| | Distribution of oligomers (%) | | | |
|---|---|---|---|---|
| | V 1 | V 2 | V 3 | Comp. |
| $C_8$ | 36.62 | 41.74 | 37.62 | 64.95 |
| $C_{12}$ | 54.32 | 51.12 | 53.22 | 32.11 |
| $C_{16}$ | 8.44 | 6.73 | 8.42 | 2.94 |
| $C_{20}$ | 0.62 | 0.41 | 0.74 | — |

The increase according to the invention of the more valuable higher $C_{12}$–$C_{20}$ oligomers in comparison with the $C_8$ portion is marked. Within the product spectrum of the $C_8$ hydrocarbons, there is also an advantageous shift in favor of the wanted dimers from 2 molecules of i-butene ("dimer") with respect to so-called "codimer", which is formed with the participation of 1-butene (Tab. 5 below).

TABLE 5

|  | V 1 | V 2 | V 3 | Comp. |
|---|---|---|---|---|
| Dimer | 99.77 | 99.83 | 99.78 | 96.00 |
| Codimer | 0.23 | 0.17 | 0.22 | 4.00 |

What is claimed is:

1. A process for oligomerizing i-butene present in a $C_4$ raffinate I, which comprises
   a) subjecting the $C_4$ raffinate I to a first hydroisomerization on a noble metal catalyst, with 30°–80° C., 5–30 bar, an LHSV of 5–30 $h^{-1}$ and a rate of 3–20 L (S.T.P.) of gaseous $H_2$ per liter of $C_4$ raffinate I which exceeds the amount of $H_2$ required to hydrogenate highly unsaturated components in the $C_4$ raffinate being employed,
   b) subjecting the hydroisomerization product of a) to fractional distillation, 5–25 bar and the temperature established at this pressure being employed, and 2-butene and n-butane being taken off as bottom product and i-butene and i-butane as overhead product,
   c) condensing the overhead product of b), dividing it into two parts and subjecting the first part to a second hydroisomerization on a noble metal catalyst, with 30°–80° C., 5–30 bar, an LHSV of 5–30 $h^{-1}$ and a rate of 0.3–5 L (S.T.P.) of gaseous $H_2$ per liter of condensate being employed and the hydroisomerization conditions in a) and c) being identical or different, and the hydroisomerization product of c) being recycled into the upper third of the fractionation column of b) and
   d) oligomerizing the second part of the condensed overhead product of b) at 30°–140° C. on an acid catalyst.

2. The process of claim 1, wherein the division of the condensed overhead product of the fractionation column is performed in such a manner that, for 1 part by volume of the condensate fed to the oligomerization, 10 to 40 parts by volume are fed to the second hydroisomerization.

3. The process of claim 2, wherein for 1 part by volume of the condensate fed to the oligomerizsation, 20 to 30 parts by volume are fed to the second hydroisomerization.

4. The process of claim 1, wherein, as hydroisomerization catalyst, use is made of Ru, Rh, Pd, Ir, Pt or a plurality thereof on a support.

5. The process of claim 4, wherein use is made of Ru, Pd, Pt or a plurality thereof on a support.

6. The process of claim 5, wherein use is made of Pd on a support.

7. The process of claim 1, wherein, for the hydroisomerization, the flow passes through the reactor equipped with the catalyst from bottom to top in flooded form.

8. The process of claim 1, wherein the LHSV in step a) is set at 7–20 $h^{-1}$.

9. The process of claim 8, wherein the LHSV in step a) is set at 7–12 $h^{-1}$.

10. The process of claim 1, wherein the LHSV in step c) is set at 10–25 $h^{-1}$.

11. The process of claim 10, wherein the LHSV in step c) is set at 15–25 $h^{-1}$.

* * * * *

UNITED STATES PATENT AND TRADEMARK OFFICE
CERTIFICATE OF CORRECTION

PATENT NO. : 5,789,643
DATED : August 4, 1998
INVENTOR(S) : Herwig, et al.

It is certified that error appears in the above-indentified patent and that said Letters Patent is hereby corrected as shown below:

Col. 8, Claim 3, Line 2    Delete "oligomerizsation" and substitute --oligomerization--

Signed and Sealed this

Twenty-eighth Day of September, 1999

Attest:

Q. TODD DICKINSON

Attesting Officer    Acting Commissioner of Patents and Trademarks